United States Patent [19]

Martin et al.

[11] Patent Number: 5,035,612
[45] Date of Patent: Jul. 30, 1991

[54] DEBONDING TIP FOR ELECTROTHERMAL DENTAL BRACKET REMOVAL

[75] Inventors: Patrick Martin, La Costa; Richard L. McMillan, San Diego, both of Calif.

[73] Assignee: Johnson & Johnson Consumer Products, Inc., New Brunswick, N.J.

[21] Appl. No.: 518,059

[22] Filed: May 2, 1990

[51] Int. Cl.⁵ .............................................. A61C 3/00
[52] U.S. Cl. .......................................... 433/3; 433/32
[58] Field of Search ..................................... 433/3, 32

[56] References Cited

U.S. PATENT DOCUMENTS

| | | | |
|---|---|---|---|
| 4,155,164 | 5/1979 | White | 433/3 |
| 4,455,138 | 6/1984 | Sheridan | 433/3 |
| 4,824,366 | 4/1989 | Hohmann et al. | 433/32 |
| 4,907,965 | 3/1990 | Martin | 433/3 |

FOREIGN PATENT DOCUMENTS

WO87/01577  3/1987  Fed. Rep. of Germany.

*Primary Examiner*—Robert P. Swiatek
*Assistant Examiner*—Nicholas D. Lucchesi
*Attorney, Agent, or Firm*—Paul A. Coletti

[57] ABSTRACT

A debonding tip for electrothermal debonding device is disclosed. This debonding tip fits around the mesio distal sides and into the saddle slot of a dental bracket. The debonding tip causes rapid heating of the dental bracket and weakens the adhesive bond used to bond brackets to teeth. With the increased viscosity, the bracket is able to be rotated around and pulled off the tooth.

10 Claims, 3 Drawing Sheets

DEBONDING TIP FOR ELECTROTHERMAL DENTAL BRACKET REMOVAL

FIELD OF THE INVENTION

This invention relates generally to removal of dental brackets. More specifically, this invention relates to the electrothermal heating of dental brackets for their removal. Most specifically, this invention relates to the use of a debonding tip wherein the debonding tip conforms to the shape of a dental bracket for heating the bracket to be removed from the teeth.

BACKGROUND OF THE INVENTION

The use of heat to remove dental brackets has become one of the more popular and accepted methods. In order to have successful dental bracket removal using heat, it is necessary to heat the bracket to a temperature where adhesive becomes loose enough in order to become viscous, and such that the user of a heating instrument can pull or pry the dental bracket from the tooth. Of course, the situation requires a very specific amount of heat to be applied to the bracket, in order that the bracket heat to a sufficient level, but that the tooth surface and pulp are not affected.

One such instrument which discloses such heating of dental brackets is Sheridan, U.S. Pat. No. 4,455,138. In Sheridan, a mechanism is used where the debonding tip is able to be placed within the archwire slot of a dental bracket and a looped cable fits around the tie wings of the dental bracket in order to pry the dental bracket from its position after the application of heat. While Sheridan was the first to demonstrate the use of heat in removing dental bracket adhesives, the Sheridan method had certain drawbacks. Most specifically, in Sheridan, the forces necessary to remove the dental bracket were unacceptable.

In Martin, U.S. Pat. No. 4,907,965, I demonstrate that the heating of a dental bracket can be accomplished while simultaneously using a prying instrument acting as a reactive base within the heating instrument. Therefore, a reactive base is placed against the tooth, the tie wings are attached to the pulling instrument attached to a spring, and the debonding tip is attached into the archwire. After heating the adhesive, the nose which creates the reactive base of the instrument pushes against the tooth while the spring pulls off the dental bracket from the tooth, as the now heated adhesive has become viscous.

While my apparatus has been shown to be quite successful, it is felt that methods and devices for removal of the dental brackets could further be refined. It has been found that the stronger the grip of the dental bracket heating mechanism on the dental bracket and the larger the surface area in which the dental bracket is heated, the quicker the adhesive becomes viscous, and therefore the less heat is exerted on the tooth. Of course, this adds to patient comfort, and usefulness of the electrothermal heating device.

SUMMARY OF THE INVENTION

It is therefore an object of the invention to provide a debonding tip which allows for increased surface area for heating a dental bracket.

It is further an object of the invention, to provide a debonding tip where the dental bracket remains firmly gripped within the debonding tip during all phases of electrothermal debonding.

It is yet another object of the invention, that the debonding tip be capable of heating the dental bracket and therefore the dental bracket adhesive, but not the tooth.

It is yet another object of the invention to provide a dental bracket debonding tip where the forces necessary to pull the bracket off the tooth remain reduced.

These and other objects of the invention are accomplished in a dental bracket removing instrument having a debonding tip contoured like the cross section of a dental bracket. The debonding tip contains a central heating portion which fits within the archwire slot of the dental bracket. It also contains a heating portion which fits around the tie wings of the dental bracket. The outer portions of the debonding tip are spring loaded so that they conform to the shape of the bracket as the debonding tip is placed on the dental bracket. After heating the dental bracket and the adhesive, the dental bracket may be pulled from the tooth. The spring force around the dental bracket keeps the bracket attached to the debonding tip at all times before, during and after heating.

These and other objects of the invention will be better understood in the attached Detailed Description of the Drawings taken in combination with the Detailed Description of the Invention.

DETAILED DESCRIPTION OF THE DRAWINGS

DETAILED DESCRIPTION OF THE INVENTION

As seen in FIGS. 1, 2, 3 and 4, there is disclosed a debonding tip 10 which forms this invention. The debonding tip 10 is attached to an electrothermal debonding device 20 generally at opening 30 located in the distal end of the debonding tip 10. The electrothermal debonding device 20 provides electrothermal heat into the debonding tip in order to heat dental bracket 1.

Figure 5:
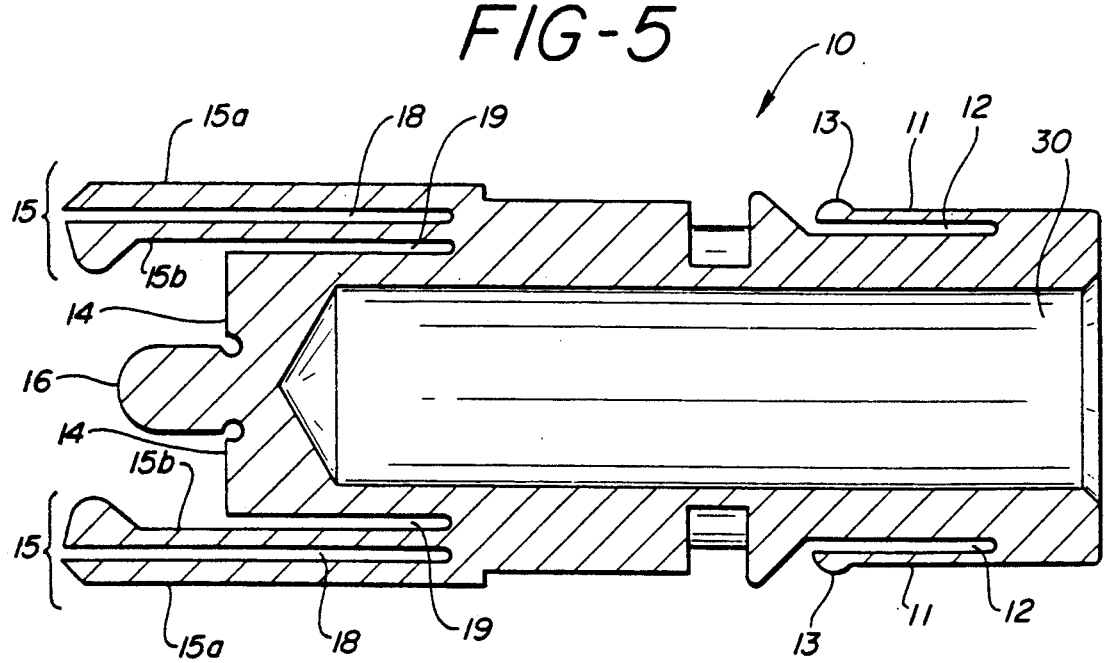
FIG. 5 is a cross section view of the debonding tip of the invention taken along lines 5—5 of FIG. 4.

As seen in FIG. 5, the debonding tip 10 contains a pair of leaf spring prongs 15, and a saddle slot ridge 16. These prongs 15 are generally configured to fit around the mesio distal sides of dental bracket 1. The saddle slot ridge 16 is configured to fit within a saddle slot of the dental bracket 1. Each of the prongs 15 contains an outside portion 15a and an inside portion 15b. The generally metallic debonding tip 10 is separated along the prong 15 by means of electrical discharge machining (EDM), creating slot 18 in each of the prongs 15. The prongs 15 are formed by virtue of electrical discharge machining to create slot 19 between prong 15 and base 14. Thus, inner surface 15b acts as a leaf spring and its spring force allows inner surface of prong 15, formed as element 15b, to be moved away from the center of the debonding tip 10. Due to the resiliency of the spring, inner surface 15b is capable of returning to its position after force is removed.

As can further be seen on FIG. 5, the rear of debonding tip 10 contains two prongs 11 separated by gap 12 which are also formed by EDM. These prongs 11 allow nodes 13 to be placed into mating slots not shown on electrothermal debracketing device 20 so that attachment 30 fits well into the electrothermal debracketing device 20.

Figure 1:
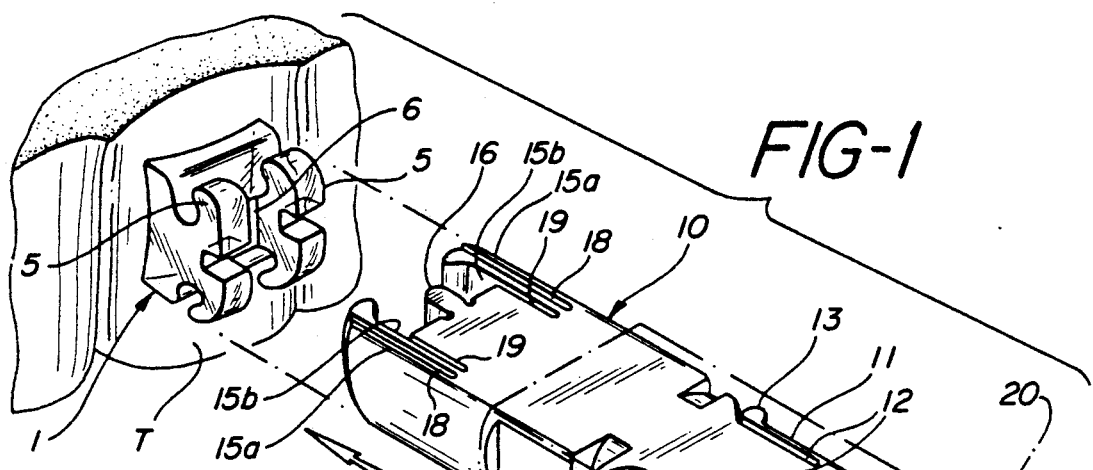
FIG. 1 is a perspective view of the debonding tip of the invention.
Figure 2:
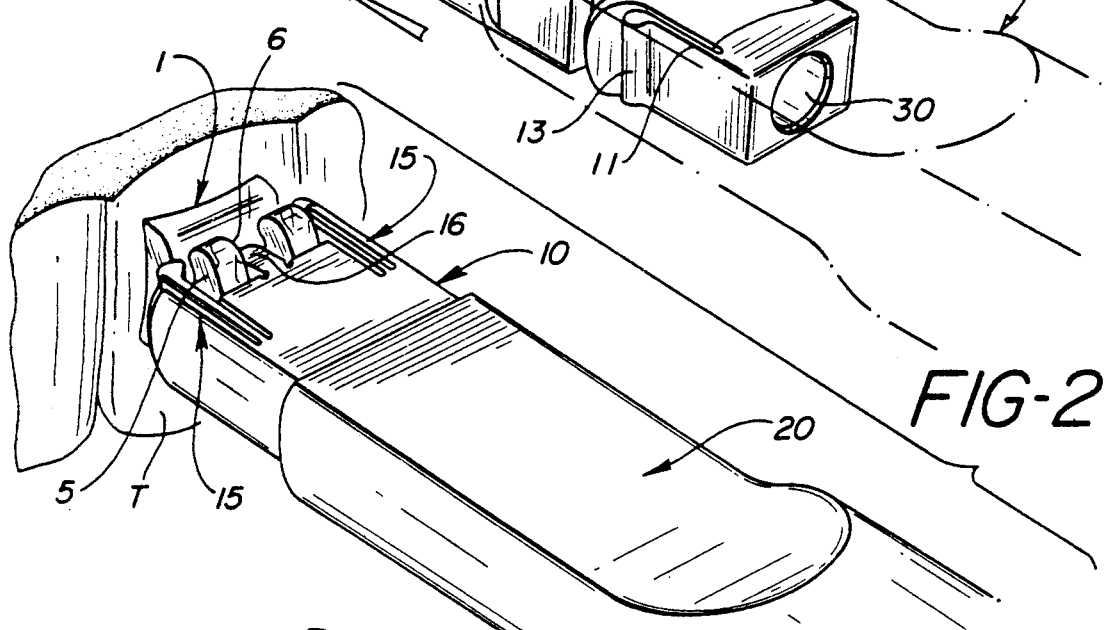
FIG. 2 is a perspective view of the debonding tip of the invention when attached to an electrothermal debracketing device.
Figure 6:
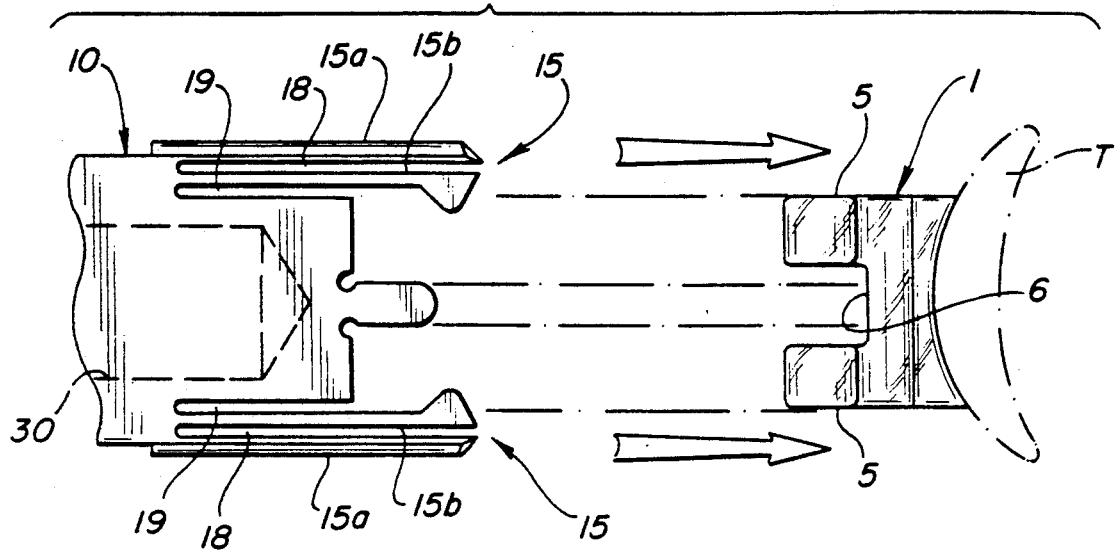
FIG. 6 is a top plan view of a debonding tip of the invention before attachment to a dental bracket.
Figure 7:
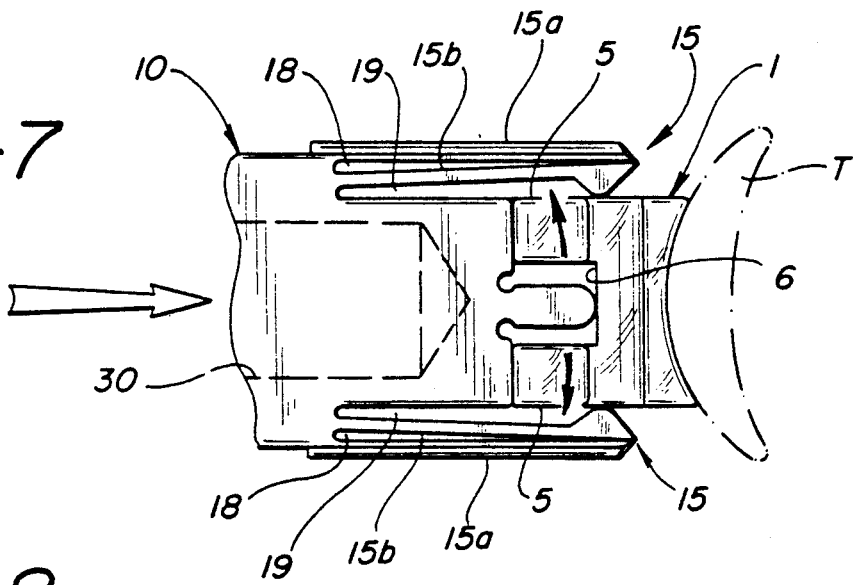
FIG. 7 is a top plan view of the invention showing the debonding tip attaching to the dental bracket.

Therefore, as seen in FIGS. 1 and 6, electrothermal debracketing device 20 incorporating debonding tip 10, is ready to be applied onto dental bracket 1 situated on tooth T. The saddle slot ridge 16 is aligned with saddle slot 6 on dental bracket 1. Each of the prongs 15 is aligned with the mesio distal sides 5 on the dental bracket 1. As seen in FIGS. 2 and 7, the dental bracket having the electrothermal debonding device 20 is placed onto dental bracket 1 so that saddle slot 6 mates with notch 16 of the electrothermal debonding tip 10. Inner surface 15b of prong 15 is caused to move away from the center of electrothermal heating device 10. Inner surface of 15b of prong 15b is stopped by outer surface 15a of prong 15, so that the inner surface 15b is caused to slip over mesio distal sides 5 of dental bracket 1.

Figure 3:
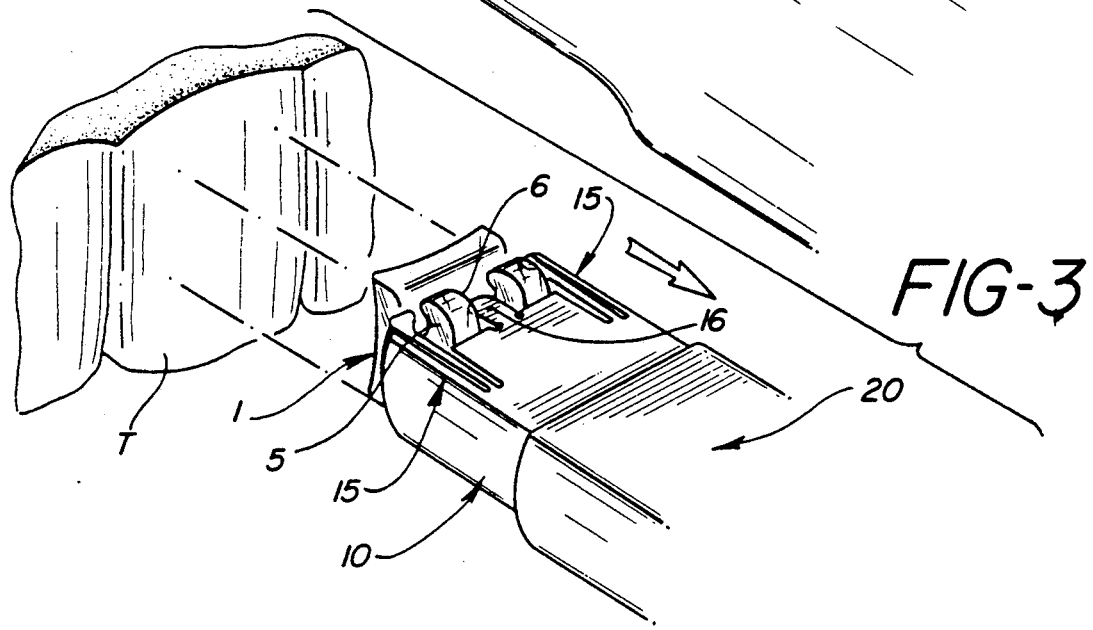
FIG. 3 is a perspective view of the debonding tip of the invention with a dental bracket attached.
Figure 4:
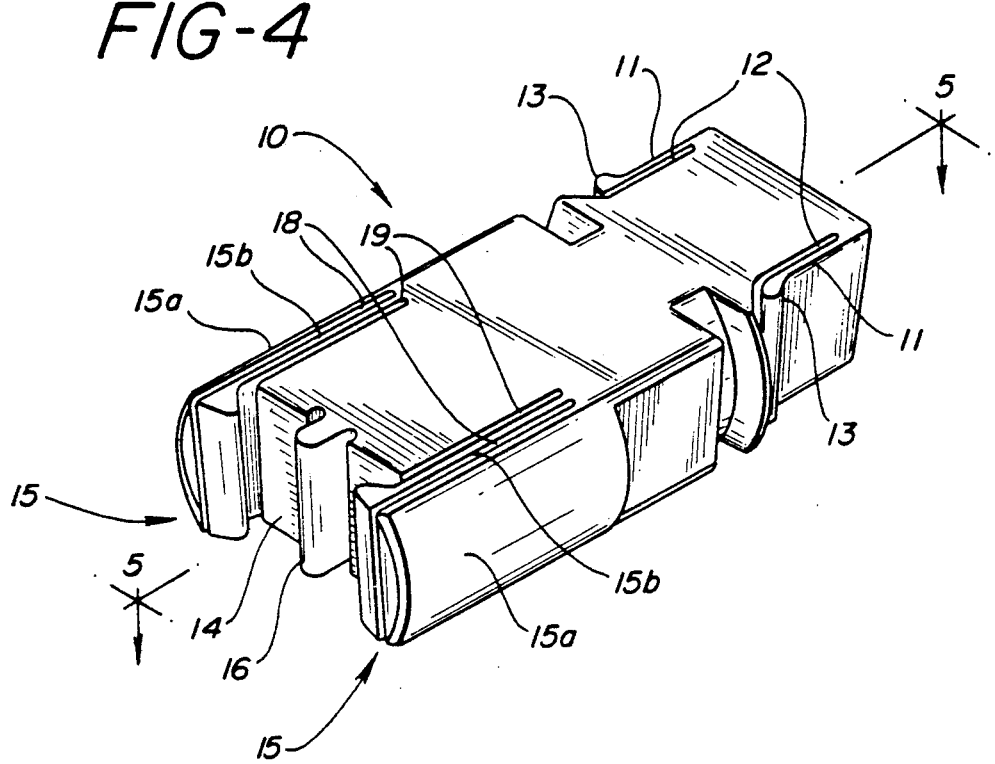
FIG. 4 is a perspective view of the front of the debonding tip of the invention.
Figure 8:
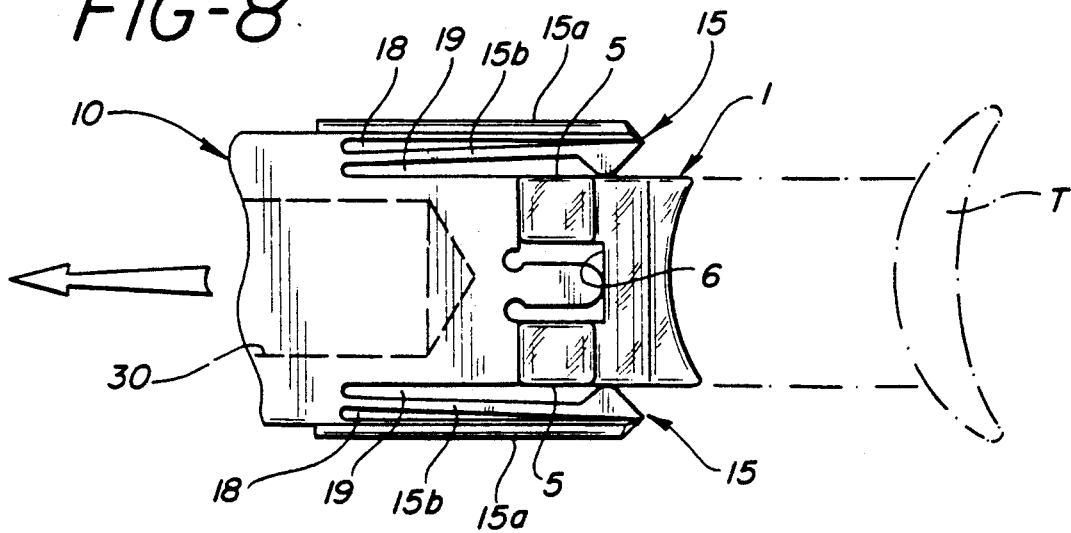
FIG. 8 is a top plan view of the invention showing the debonding tip attached to the dental bracket.

Further, as seen in FIGS. 3 and 8, the dental bracket has now been attached to the electrothermal debonding tip 10. Inner surface 15b of prongs 15 has fallen into place on each of the sides 5 of dental bracket 1. Also, the notch 16 is firmly seated within saddle slot 6. Once the debonding tip has caused the dental bracket 1 to be heated enough to cause the adhesive attaching dental bracket 1 to the tooth T to become viscous, the dental bracket is able to be removed, as seen in FIG. 3, by torsional force.

This improved debonding tip 10 allows heating to be accomplished in as quick a time period as 2 to 3 seconds as the dental brackets increase in heat rapidly, and cause the adhesive to become softened. The improved surface area contact is responsible for such quick heating. It has been found that the adhesive heats to about 180° C., which is well below any pain threshold for humans, but is enough to create a softened, loose adhesive.

Therefore, this new debonding tip can be used in conjunction with former methods of heating dental brackets in order to electrothermally debond them from teeth. Especially useful is the fact that because prongs 15 are securely fastened to dental bracket 1 such that inner surfaces 15b are placed firmly on mesio distal sides 5, in, at a minimum, a press fit. This allows a torsional force to be placed on bracket 1 without worry of the debonding tip 10 becoming loose from dental bracket 1 during or after debonding from the surface of the tooth.

As it will be appreciated by those skilled in the art, it is necessary that the debonding tip of the present invention be configured to thoroughly enclose the dental bracket so that it is this which is intended from the present disclosure. Therefore, this present invention can be best described by the attached claims and their equivalents.

What is claimed is:

1. A heating element comprising a debonding tip for electrothermally debonding a dental bracket adhesively attached to a tooth, said bonding tip conforming to the surface of the dental bracket in a mating relationship with said bracket surface and further including prongs attachable around the tie wings of a dental bracket and wherein said prongs each comprise a leaf spring which fits on the mesio-distal sides of the bracket, and a rigid outer member against which said leaf spring is forced when placed on said bracket.

2. The element of claim 1 wherein said bracket and said element interlock with one another.

3. The element of claim 2 wherein said bracket contains a saddle slot and aid element contains a ridge which fits within said slot.

4. The element of claim 3 wherein said debonding tip has electrothermal heat applied to it, and the heat envelops said bracket on the surface of said said bracket.

5. The element of claim 4 wherein said tip is metallic.

6. A heating element comprising a debonding tip attachable to an electrothermal debracketing device for supplying electrothermal heat to said bracket, comprising:
a pair of prongs for placement around said bracket, said prongs each containing a rigid outer member separated by a leaf spring said, leaf spring on each of said prongs configured to be spaced apart at a distance slightly less than the dimension of said bracket to exert force on said bracket when said bracket is placed between said springs by urging each of said springs against each said rigid outer member to hold said tip on said bracket; and
a base conforming to the brace of said bracket.

7. The element of claim 6 where said base includes a ridge for insertion into a saddle slot of a dental bracket.

8. The element of claim 6 wherein said springs are leaf springs.

9. The element of claim 6 wherein said tip is metallic.

10. A method for removing dental bracket adhesively attached to a tooth, comprising:
clamping said bracket with a heating element comprising a debonding tip, said element conforming to the surface of said adi bracket and containing a pair of prongs, said prongs including ridge members resiliently controlling a pair of leaf springs which old said tip on said bracket;
applying heat to said element such that said bracket and achieve are heated; and
rotating said bracket from said tooth when said adhesive is loosened by exerting a torsional force on said element.

* * * * *

UNITED STATES PATENT AND TRADEMARK OFFICE
CERTIFICATE OF CORRECTION

PATENT NO. : 5,035,612

DATED : July 30, 1991

INVENTOR(S) : Patrick Martin and Richard L. McMillan

It is certified that error appears in the above-identified patent and that said Letters Patent is hereby corrected as shown below:

Column 4, line 51 after "said" remove "adi".

Column 4, line 54 "old" should be "hold".

Column 4, line 56 "achieve" should be "adhesive".

Signed and Sealed this

Twenty-third Day of March, 1993

Attest:

STEPHEN G. KUNIN

*Attesting Officer*     *Acting Commissioner of Patents and Trademarks*